United States Patent
Tonomura et al.

(10) Patent No.: US 6,245,925 B1
(45) Date of Patent: Jun. 12, 2001

(54) HYDROSILYLATION OF 4-VINYL-1-CYCLOHEXENE

(75) Inventors: Yoichi Tonomura; Tohru Kubota; Mikio Endo, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/627,074

(22) Filed: Jul. 27, 2000

(30) Foreign Application Priority Data

Jul. 28, 1999 (JP) .................................................. 11-213481

(51) Int. Cl.$^7$ ..................................................... C07F 7/08
(52) U.S. Cl. ............................................. 556/431; 556/479
(58) Field of Search ..................................... 556/431, 479

(56) References Cited

U.S. PATENT DOCUMENTS

| 2,823,218 | * | 2/1958 | Speier et al. | 556/479 |
| 5,514,827 | * | 5/1996 | Petty | 556/431 |
| 5,527,936 | | 6/1996 | Dindi et al. . | |
| 5,726,336 | * | 3/1998 | Jung et al. | 556/431 |

OTHER PUBLICATIONS

Japanese Publication of International Patent Application No. 11-500129, 1996.

Comprehensive Handbook on Hydrosilylation, p. 108, 1968.

* cited by examiner

Primary Examiner—Paul F. Shaver
(74) Attorney, Agent, or Firm—Millen, White, Zelano & Branigan, P.C.

(57) ABSTRACT

By reacting 4-vinyl-1-cyclohexene with a hydrogenchlorosilane compound in the presence of a platinum catalyst to give a reaction solution containing a monosilyl compound, removing the residual 4-vinyl-1-cyclohexene and isomers thereof from the reaction solution, and reacting the monosilyl compound again with the hydrogenchlorosilane compound, an organic silicon compound in which the two double bonds in 4-vinyl-1-cyclohexene have been hydrosilylated is produced in high yields.

13 Claims, No Drawings

HYDROSILYLATION OF 4-VINYL-1-CYCLOHEXENE

This invention relates to a process of hydrosilylating 4-vinyl-1-cyclohexene in the presence of a platinum catalyst to produce an organic silicon compound of the following general formula (2):

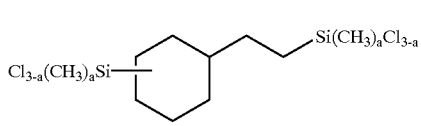

wherein "a" is equal to 0, 1 or 2.

BACKGROUND OF THE INVENTION

Because of a cyclohexane ring within its molecule, the organosilicon compound of formula (2) has a high hardness and scratch resistance and is useful as a coupling agent to be added to paints for use in automobile painting and building painting and adhesives. The compound is also useful as an intermediate to an alkoxysilane coupling agent.

The method which is believed best for producing an organosilicon compound of formula (2) is by starting with 4-vinyl-1-cyclohexene and adding a hydrogenchlorosilane compound to the two double bonds therein. For this method, the use of a radical initiator is proposed in Japanese Publication of International Patent Application No. 11-500129. Since the radical initiator used herein has the potential of explosion, this method is hazardous and difficult to control the reaction. The method is cumbersome since the radical initiator must be supplemented in sequence. Additionally, the reaction solution contains only about 30% of (2-trichlorosilylethyl)trichlorosilylcyclohexane which is a disilylated product, indicating low reactivity. The method is not advantageous for industrial use.

An alternative method is by reacting 4-vinyl-1-cyclohexene with a hydrogenchlorosilane compound in the presence of a platinum catalyst. It is reported in Comprehensive Handbook on Hydrosilylation, page 108, that reaction occurs only at the double bond of vinyl group while the double bond within the ring remains intact.

SUMMARY OF THE INVENTION

An object of the invention is to provide a process for producing an organic silicon compound of the general formula (2) in a safe, efficient, and economical manner.

The invention is predicated on the following finding. When 4-vinyl-1-cyclohexene is reacted with a hydrogenchlorosilane compound of the general formula (1), there is obtained a reaction solution containing a monosilyl compound of the general formula (3) as well as the residual 4-vinyl-1-cyclohexene and isomers thereof. Thereafter, the residual 4-vinyl-1-cyclohexene and isomers thereof are removed from the reaction solution, and preferably the monosilyl compound is isolated from the reaction solution. The monosilyl compound from which unreacted 4-vinyl-1-cyclohexene and isomers thereof have been removed is reacted again with the hydrogenchlorosilane compound of the general formula (1). Then, quite unexpectedly, the hydrogenchlorosilane compound induces addition reaction to the double bond in the cyclohexene ring whereby there is obtained an organic silicon compound of the general formula (2) in which the hydrogenchlorosilane is added to each of the two double bonds in 4-vinyl-1-cyclohexene.

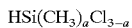

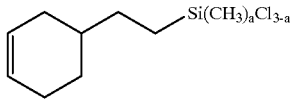

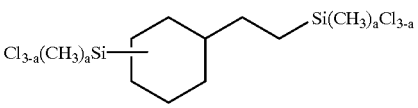

Note that "a" is equal to 0, 1 or 2.

According to the invention, there is provided a process for hydrosilylating 4-vinyl-1-cyclohexene, comprising the steps of reacting 4-vinyl-1-cyclohexene with a hydrogenchlorosilane compound of the general formula (1) in the presence of a platinum catalyst, obtaining a reaction solution containing a monosilyl compound of the general formula (3); removing the residual 4-vinyl-1-cyclohexene and isomers thereof from the reaction solution, preferably isolating the monosilyl compound; and reacting the monosilyl compound again with the hydrogenchlorosilane compound of the general formula (1) to form an organic silicon compound of the general formula (2).

DESCRIPTION OF THE PREFERRED EMBODIMENT

The process of the invention involves the steps of (i) reacting 4-vinyl-1-cyclohexene with a hydrogenchlorosilane compound of the general formula (1) in the presence of a platinum catalyst, obtaining a reaction solution containing a monosilyl compound of the general formula (3), (ii) removing the residual 4-vinyl-1-cyclohexene and isomers thereof from the reaction solution, and (iii) reacting the monosilyl compound again with the hydrogenchlorosilane compound of the general formula (1) to form an organic silicon compound of the general formula (2).

The hydrogenchlorosilane compound used herein is of the following general formula (1):

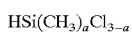

wherein "a" is equal to 0, 1 or 2. Specific examples are trichlorosilane, methyldichlorosilane and dimethylchlorosilane.

In steps (i) and (iii), the mixing ratio of the hydrogenchlorosilane compound to 4-vinyl-1-cyclohexene is preferably adjusted from the reactivity and productivity standpoints such that for each of the first and second stages of reaction, 0.5 to 2.0 mol, and especially 0.8 to 1.2 mol of the hydrogenchlorosilane compound is available per mol of 4-vinyl-1-cyclohexene.

The platinum catalyst used is not critical. Exemplary catalysts are chloroplatinic acid, alcohol solutions of chloroplatinic acid, platinum complexes such as platinum with divinyltetramethyldisiloxane, and platinum-carrying catalysts such as platinum on carbon and platinum on silica. The amount of the platinum catalyst used is preferably adjusted from the reactivity and productivity standpoints such that for each of the first and second stages of reaction, 0.000001 to 0.01 mol, and especially 0.00001 to 0.001 mol of the platinum catalyst is available per mol of 4-vinyl-1-cyclohexene.

The reaction temperature is not critical although a temperature of 0 to 150° C., especially room temperature to 120° C. is preferred from the reactivity standpoint for each of the first and second stages of reaction.

A solvent may be used although the reaction can proceed without a solvent. Useful solvents include hydrocarbon solvents such as pentane, hexane, cyclohexane, benzene and toluene, ether solvents such as diethyl ether, tetrahydrofuran and dioxane, ester solvents such as ethyl acetate and butyl acetate, aprotic polar solvents such as acetonitrile, and chlorinated hydrocarbon solvents such as dichloromethane and chloroform. These solvents may be used alone or in admixture of two or more.

In step (ii), the residual 4-vinyl-1-cyclohexene and isomers thereof are removed from the reaction solution by several procedures. One procedure is by distilling the reaction solution for isolating the monosilyl compound of the general formula (3) shown below. Alternatively, the reaction solution is heated, optionally in vacuum, allowing 4-vinyl-1-cyclohexene and isomers thereof to distill out. From the reactivity standpoint, distillative isolation is preferred.

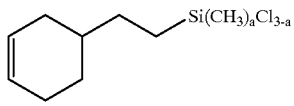
(3)

Note that "a" is equal to 0, 1 or 2.

According to the invention, the two stages of reaction are effected to produce an organosilicon compound of the general formula (2):

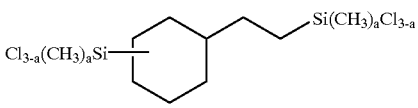
(2)

wherein "a" is equal to 0, 1 or 2. Illustrative examples of the compound include (2-trichlorosilylethyl)trichlorosilylcyclohexane, (2-methyldichlorosilylethyl)methyldichlorosilylcyclohexane, and (2-dimethylchlorosilylethyl)dimethylchlorosilylcyclohexane.

EXAMPLE

Examples of the invention are given below by way of illustration and not by way of limitation.

Example 1

(2-trichlorosilylethyl)trichlorosilylcyclohexane (1) Isolation of 4-(2-trichlorosilylethyl)-1-cyclohexene A flask equipped with a stirrer, reflux condenser, dropping funnel and thermometer was charged with 432.8 g (4.0 mol) of 4-vinyl-1-cyclohexene and 0.4 g of a 20 wt % isopropanol solution of chloroplatinic acid, which were heated at 80° C. After the internal temperature became constant, 596.2 g (4.4 mol) of trichlorosilane was added dropwise over 4 hours. After the completion of addition, the reaction solution was stirred for one hour at 80° C. The reaction solution was distilled, collecting 925.9 g of 4-(2-trichlorosilylethyl)-1-cyclohexene as a fraction having a boiling point of 106–109° C./10 mmHg (yield 95.0%).

(2) Synthesis of (2-trichlorosilylethyl)trichlorosilylcyclohexane

A flask equipped with a stirrer, reflux condenser, dropping funnel and thermometer was charged with 121.8 g (0.50 mol) of 4-(2-trichlorosilylethyl)-1-cyclohexene and 0.1 g of a 20 wt % isopropanol solution of chloroplatinic acid, which were heated at 80° C. After the internal temperature became constant, 74.5 g (0.55 mol) of trichlorosilane was added dropwise over 10 hours. After the completion of addition, the reaction solution was stirred for 8 hours at 80° C. The reaction solution was distilled, collecting 157.3 g of (2-trichlorosilylethyl)trichlorosilylcyclohexane as a fraction having a boiling point of 122–126° C./0.1 mmHg (yield 83.0%).

Example 2

(2-methyldichlorosilylethyl)methyldichlorosilylcyclohexane (1) Isolation of 4-(2-methyldichlorosilylethyl)-1-cyclohexene A flask equipped with a stirrer, reflux condenser, dropping funnel and thermometer was charged with 108.2 g (1.0 mol) of 4-vinyl-1-cyclohexene and 0.05 g of a 20 wt % isopropanol solution of chloroplatinic acid, which were heated at 80° C. After the internal temperature became constant, 126.5 g (1.1 mol) of methyldichlorosilane was added dropwise over 3 hours. After the completion of addition, the reaction solution was stirred for one hour at 80° C. The reaction solution was distilled, collecting 205.0 g of 4-(2-methyldichlorosilylethyl)-1-cyclohexene as a fraction having a boiling point of 97–99° C./5 mmHg (yield 91.8%).

(2) Synthesis of (2-methyldichlorosilylethyl)methyldichlorosilylcyclohexane

A flask equipped with a stirrer, reflux condenser, dropping funnel and thermometer was charged with 111.6 g (0.50 mol) of 4-(2-methyldichlorosilylethyl)-1-cyclohexene and 0.1 g of a 20 wt % isopropanol solution of chloroplatinic acid, which were heated at 80° C. After the internal temperature became constant, 63.3 g (0.55 mol) of methyldichlorosilane was added dropwise over 5 hours. After the completion of addition, the reaction solution was stirred for 8 hours at 80° C. The reaction solution was distilled, collecting 136.0 g of (2-methyldichlorosilylethyl)methyldichlorosilylcyclohexane as a fraction having a boiling point of 122–124° C./0.1 mmHg (yield 80.4%).

Comparative Example 1

A flask equipped with a stirrer, reflux condenser, dropping funnel and thermometer was charged with 27.1 g (0.25 mol) of 4-vinyl-1-cyclohexene and 0.02 g of a 20 wt % isopropanol solution of chloroplatinic acid, which were heated at 80° C. After the internal temperature became constant, 37.3 g (0.27 mol) of trichlorosilane was added dropwise over 3 hours. After the completion of addition, the reaction solution was stirred for one hour at 80° C. It was found that 4-(2-trichlorosilylethyl)-1-cyclohexene was formed as a result of hydrosilylation of the vinyl group moiety of 4-vinyl-1-cyclohexene. To this reaction solution were added 0.05 g of a 20 wt % isopropanol solution of chloroplatinic acid and 4.0 g of trichlorosilane. The solution was stirred for 2 hours at 80° C. There was formed no (2-trichlorosilylethyl)trichlorosilylcyclohexane resulting from hydrosilylation of the double bond in the cyclohexene ring, and trichlorosilane remained unreacted.

Comparative Example 2

A flask equipped with a stirrer, reflux condenser, dropping funnel and thermometer was charged with 27.1 g (0.25 mol) of 4-vinyl-1-cyclohexene and 0.02 g of a 20 wt % isopropanol solution of chloroplatinic acid, which were heated at 80° C. After the internal temperature became constant, 31.6 g (0.27 mol) of methyldichlorosilane was added dropwise over 3 hours. After the completion of addition, the reaction solution was stirred for one hour at 80° C. It was found that 4-(2-methyldichlorosilylethyl)-1-cyclohexene was formed as a result of hydrosilylation of the vinyl group moiety of 4-vinyl-1-cyclohexene. To this reaction solution were added 0.05 g of a 20 wt % isopropanol solution of chloroplatinic acid and 10.0 g of methyldichlorosilane. The solution was stirred for one hour at 80° C. It was found that (2-methyldichlorosilylethyl)methyldichlorosilylcyclohexane resulting from hydrosilylation of the double bond in the cyclohexene ring formed at a conversion of 9.4%, but most methyldichlorosilane remained unreacted. The reaction solution was ripened for a further 3 hours at 80° C., but the conversion remained unchanged, that is, the methyldichlorosilane remained intact.

There has been described a process for hydrosilylating 4-vinyl-1-cyclohexene wherein reaction proceeds without stopping at one stage so that a product in which the two double bonds in 4-vinyl-1-cyclohexene have been hydrosilylated is obtainable in high yields. The process ensures safe, effective and economical hydrosilylation, with great industrial benefits.

Japanese Patent Application No. 11-213481 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:
1. A process for hydrosilylating 4-vinyl-1-cyclohexene, comprising the steps of reacting 4-vinyl-1-cyclohexene with a hydrogenchlorosilane compound of the following formula (1):

(1)

wherein "a" is equal to 0, 1 or 2, in the presence of a platinum catalyst, obtaining a reaction solution containing a monosilyl compound of the following formula (3):

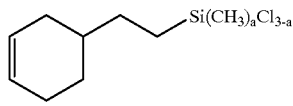

(3)

wherein "a" is as defined above, removing the residual 4-vinyl-1-cyclohexene and isomers thereof from the reaction solution, and reacting the monosilyl compound again with the hydrogenchlorosilane compound of the formula (1) to form an organic silicon compound of the following formula (2):

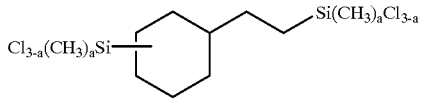

(2)

wherein "a" is as defined above.

2. A process for hydrosilylating 4-vinyl-1-cyclohexene, comprising the steps of reacting 4-vinyl-1-cyclohexene with a hydrogenchlorosilane compound of the following formula (1):

(1)

wherein "a" is equal to 0, 1 or 2, in the presence of a platinum catalyst, obtaining a reaction solution containing a monosilyl compound of the following formula (3):

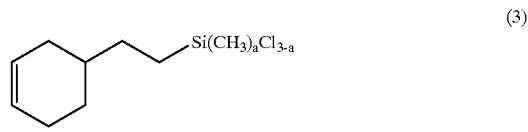

(3)

wherein "a" is as defined above, distilling the reaction solution to isolate the monosilyl compound of the formula (3), and reacting the monosilyl compound again with the hydrogenchlorosilane compound of the formula (1) to form an organic silicon compound of the following formula (2):

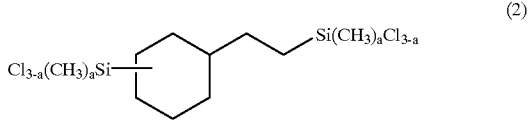

(2)

wherein "a" is as defined above.

3. The process of claim 1, wherein 0.5 to 2.0 mol of the hydrogenchlorosilane compound of formula (I) is provided per mol of the 4-vinyl-1-cyclohexene in the first reaction step and 0.5 to 2.0 mol of the hydrogenchlorosilane compound of formula (I) is provided per mol of the monosilyl compound of formula (3) in the next reaction step.

4. The process of claim 2, wherein 0.5 to 2.0 mol of the hydrogenchlorosilane compound of formula (I) is provided per mol of the 4-vinyl-1-cyclohexene in the first reaction step and 0.5 to 2.0 mol of the hydrogenchlorosilane compound of formula (I) is provided per mol of the monosilyl compound of formula (3) in the next reaction step.

5. The process of claim 1, wherein 0.8 to 1.2 mol of the hydrogenchlorosilane compound of formula (I) is provided per mol of the 4-vinyl-1-cyclohexene in the first reaction step and 0.5 to 2.0 mol of the hydrogenchlorosilane compound of formula (I) is provided per mol of the monosilyl compound of formula (3) in the next reaction step.

6. The process of claim 2, wherein 0.8 to 1.2 mol of the hydrogenchlorosilane compound of formula (I) is provided per mol of the 4-vinyl-1-cyclohexene in the first reaction step and 0.5 to 2.0 mol of the hydrogenchlorosilane compound of formula (I) is provided per mol of the monosilyl compound of formula (3) in the next reaction step.

7. The process of claim 1, wherein both reaction steps are conducted at a temperature from 0 to 150°C.

8. The process of claim 2, wherein both reaction steps are conducted at a temperature from 0 to 150°C.

9. The process of claim 2, wherein both reaction steps are conducted at a temperature from room temperature to 120°C.

10. The process of claim 2, wherein both reaction steps are conducted at a temperature from room temperature to 120°C.

11. The process of claim 1, wherein the process is conducted in the presence of a solvent.

12. The process of claim 2, wherein the process is conducted in the presence of a solvent.

13. The process of claim 1, wherein removing the residual 4-vinylcyclohexene and isomers thereof is conducted by heating in the presence of a vacuum.

* * * * *